(12) United States Patent
Young, Sr. et al.

(10) Patent No.: US 6,270,893 B1
(45) Date of Patent: *Aug. 7, 2001

(54) COATED FIBER PRODUCT WITH ADHERED SUPER ABSORBENT PARTICLES

(75) Inventors: Richard H. Young, Sr., Puyallup; Amar N. Neogi, Seattle; Michael R. Hansen, Everett, all of WA (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/207,393

(22) Filed: Mar. 7, 1994

Related U.S. Application Data

(63) Continuation of application No. 07/890,040, filed on May 27, 1992, now abandoned, which is a continuation of application No. 07/326,188, filed on Mar. 20, 1989, now Pat. No. 5,230,959.

(51) Int. Cl.[7] .................................................. D02G 3/00

(52) U.S. Cl. ......................... 428/372; 428/359; 428/375; 428/373; 428/393; 442/59; 442/330; 442/333

(58) Field of Search ................................. 428/457, 359, 428/378, 361, 372, 373, 374, 224, 288, 298, 375, 393; 442/59, 330, 361, 414, 333

(56) References Cited

U.S. PATENT DOCUMENTS

| | | |
|---|---|---|
| 2,601,597 | 6/1952 | Daniel, Jr. et al. . |
| 2,746,608 | 5/1956 | Briggs .................................. 210/205 |
| 2,757,150 | 7/1956 | Heritage .............................. 260/17.2 |
| 2,950,752 | 8/1960 | Watson et al. ............................ 154/1 |
| 2,953,187 | 9/1960 | Francis, Jr. ............................. 154/29 |
| 3,010,161 | 11/1961 | Duvall .................................... 19/156 |
| 3,021,242 | 2/1962 | Touey .................................... 156/180 |
| 3,059,313 | 10/1962 | Harmon ................................... 28/80 |
| 3,070,095 | 12/1962 | Torr .................................... 128/284 |
| 3,081,207 | 3/1963 | Fox ....................................... 154/44 |
| 3,087,833 | 4/1963 | Drelich .................................. 117/38 |
| 3,327,708 | 6/1967 | Sokolowski .......................... 128/156 |
| 3,344,789 | 10/1967 | Arnold et al. ....................... 128/287 |
| 3,361,632 | 1/1968 | Ross et al. ............................. 167/83 |
| 3,377,302 | 4/1968 | Gugliemelli et al. ................ 260/17.4 |
| 3,395,201 | 7/1968 | Kalwaites ............................... 264/45 |
| 3,425,971 | 2/1969 | Gugliemelli et al. ............... 260/17.4 |

(List continued on next page.)

FOREIGN PATENT DOCUMENTS

| | | |
|---|---|---|
| 729513 | 6/1962 | (CA) . |
| 806352 | 4/1964 | (CA) . |
| 813616 | 12/1965 | (CA) . |
| 841940 | 12/1965 | (CA) . |
| 953 890 | 9/1974 | (CA) . |

(List continued on next page.)

OTHER PUBLICATIONS

Amosov et al., "Aluminum hydroxy compounds—binders for dry–process paper," *Izv. VUZ, Lesnoi Zh.*, 6:72–76 (1986).

Blanchard and Reinhart, "Dyeing of Crosslinked Cotton Containing Glycol Additives," *U.S. Dept. of Agriculture*, New Orleans, 24:13–17 (Jan. 1992).

Burkholder, "Absorbent Polymers—A New Concept in Fluid Absorption," *The Dow Chemical Company Designed Products Laboratory*, Midland, Michigan, pp. 73–79 (1973).

(List continued on next page.)

*Primary Examiner*—William Krynski
*Assistant Examiner*—J. M. Gray
(74) *Attorney, Agent, or Firm*—Christensen O'Connor Johnson Kindness PLLC

(57) ABSTRACT

A fiber product of discontinuous fibers coated with a binder containing carboxyl groups and solid particles of superabsorbent material adhered to the fibers by the carboxyl group containing binder.

14 Claims, 2 Drawing Sheets

U.S. PATENT DOCUMENTS

| | | | |
|---|---|---|---|
| 3,490,454 | 1/1970 | Goldfarb et al. | 128/285 |
| 3,494,992 | 2/1970 | Wiegand | 264/121 |
| 3,521,638 | 7/1970 | Parrish | 128/284 |
| 3,554,788 | 1/1971 | Fechillas | 117/140 |
| 3,577,312 | 5/1971 | Videen et al. | 162/148 |
| 3,616,002 | 10/1971 | Paquette | 156/180 |
| 3,661,154 | 5/1972 | Torr | 128/284 |
| 3,661,632 | 5/1972 | Gagliardi et al. | 117/143 A |
| 3,669,103 | 6/1972 | Harper et al. | 128/156 |
| 3,670,731 | 6/1972 | Harmon | 128/284 |
| 3,671,296 | 6/1972 | Funakoshi et al. | 117/100 B |
| 3,672,945 | 6/1972 | Taylor | 117/100 B |
| 3,673,021 | 6/1972 | Joa | 156/62.4 |
| 3,687,749 | 8/1972 | Reinhall | 156/62.4 |
| 3,692,622 | 9/1972 | Dunning | 161/124 |
| 3,734,471 | 5/1973 | Engels | 259/6 |
| 3,745,060 | 7/1973 | Jumentier et al. | 161/170 |
| 3,752,733 | 8/1973 | Graham et al. | 161/170 |
| 3,765,971 | 10/1973 | Fleissner | 156/62.2 |
| 3,766,922 | 10/1973 | Krusko | 128/284 |
| 3,775,210 | 11/1973 | Paquette et al. | 156/181 |
| 3,777,758 | 12/1973 | Mesek et al. | 128/284 |
| 3,788,936 | 1/1974 | Brock et al. | 161/148 |
| 3,791,783 | 2/1974 | Damon et al. | 425/82 |
| 3,804,092 | 4/1974 | Tunc | 128/284 |
| 3,808,088 | 4/1974 | Knechtges et al. | 161/148 |
| 3,810,841 | 5/1974 | Richter | 252/91 |
| 3,836,412 | 9/1974 | Boustany et al. | 156/62.2 |
| 3,850,601 | 11/1974 | Stapleford et al. | 65/3 |
| 3,868,955 | 3/1975 | Steiger et al. | 128/296 |
| 3,886,941 | 6/1975 | Duane et al. | 128/287 |
| 3,888,256 | 6/1975 | Studinger | 128/296 |
| 3,888,257 | 6/1975 | Cook et al. | 128/296 |
| 3,901,236 | 8/1975 | Assarsson et al. | 128/284 |
| 3,903,889 | 9/1975 | Torr | 128/287 |
| 3,908,659 | 9/1975 | Wehrmeyer et al. | 128/287 |
| 3,914,498 | 10/1975 | Videen | 428/290 |
| 3,916,825 | 11/1975 | Schnitzler et al. | 118/303 |
| 3,923,592 | 12/1975 | George et al. | 162/168 |
| 3,942,729 | 3/1976 | Fredriksson | 241/38 |
| 3,949,035 | 4/1976 | Dunning et al. | 264/90 |
| 3,967,005 | 6/1976 | Cattaneo | 427/202 |
| 3,974,307 | 8/1976 | Bowen | 427/212 |
| 3,978,257 | 8/1976 | Ring | 428/137 |
| 3,991,225 | 11/1976 | Blouin | 427/3 |
| 3,991,237 | 11/1976 | Topfl et al. | 427/386 |
| 3,992,558 | 11/1976 | Smith-Johannesen et al. | 427/213 |
| 4,006,706 | 2/1977 | Lödige et al. | 118/303 |
| 4,006,887 | 2/1977 | Engels | 259/9 |
| 4,007,083 | 2/1977 | Ring et al. | 162/101 |
| 4,009,313 | 2/1977 | Crawford et al. | 428/290 |
| 4,010,308 | 3/1977 | Wiczer | 428/372 |
| 4,015,830 | 4/1977 | Lödige et al. | 259/25 |
| 4,035,217 | 7/1977 | Kennette et al. | 156/279 |
| 4,039,645 | 8/1977 | Coyle | 264/118 |
| 4,055,180 | 10/1977 | Karami | 128/287 |
| 4,061,268 | 12/1977 | DeMaster | 238/14 |
| 4,062,451 | 12/1977 | Gander | 206/524.2 |
| 4,071,636 | 1/1978 | Nishino et al. | 427/2 |
| 4,100,328 | 7/1978 | Gallagher | 428/407 |
| 4,102,340 | 7/1978 | Mesek et al. | 128/287 |
| 4,103,062 | 7/1978 | Aberson et al. | 428/283 |
| 4,111,730 | 9/1978 | Balatinecz | 156/62.2 |
| 4,122,074 | 10/1978 | Pepe et al. | 260/46.5 E |
| 4,129,132 | 12/1978 | Butterworth et al. | 128/287 |
| 4,143,975 | 3/1979 | Lödige et al. | 366/147 |
| 4,153,488 | 5/1979 | Wiegand | 156/62.2 |
| 4,160,059 | 7/1979 | Samejima | 428/288 |
| 4,168,919 | 9/1979 | Rosen et al. | 366/173 |
| 4,183,997 | 1/1980 | Stofko | 428/326 |
| 4,187,342 | 2/1980 | Holst et al. | 428/283 |
| 4,188,130 | 2/1980 | Engels | 366/228 |
| 4,191,224 | 3/1980 | Bontrager et al. | 141/100 |
| 4,193,700 | 3/1980 | Wirz | 366/156 |
| 4,232,674 | 11/1980 | Melican | 128/287 |
| 4,241,133 | 12/1980 | Lund et al. | 428/326 |
| 4,241,692 | 12/1980 | Van Hijfte et al. | 118/303 |
| 4,242,241 | 12/1980 | Rosen et al. | 260/17.2 |
| 4,248,685 | 2/1981 | Beede et al. | 204/159.22 |
| 4,250,660 | 2/1981 | Kitamura et al. | 47/57.6 |
| 4,252,844 | 2/1981 | Nesgood et al. | 427/213 |
| 4,261,943 | 4/1981 | McCorsley, III | 264/136 |
| 4,282,121 | 8/1981 | Goodrich | 260/17.4 GC |
| 4,289,513 | 9/1981 | Brownhill et al. | 55/387 |
| 4,289,536 | 9/1981 | Dereser | 106/99 |
| 4,297,253 | 10/1981 | Sorbier | 260/17.3 |
| 4,302,488 | 11/1981 | Lowi, Jr. | 427/149 |
| 4,320,166 | 3/1982 | Endo et al. | 428/283 |
| 4,320,715 | 3/1982 | Maloney et al. | 118/303 |
| 4,323,625 | 4/1982 | Coran et al. | 428/361 |
| 4,324,706 | 4/1982 | Tabe et al. | 523/149 |
| 4,337,722 | 7/1982 | Debayeux et al. | 118/303 |
| 4,354,450 | 10/1982 | Nagahama et al. | 118/303 |
| 4,360,545 | 11/1982 | Maloney et al. | 427/212 |
| 4,364,992 | 12/1982 | Ito et al. | 428/283 |
| 4,370,945 | 2/1983 | Beckschulte et al. | 118/303 |
| 4,379,194 | 4/1983 | Clarke et al. | 428/203 |
| 4,379,196 | 4/1983 | Halper | 428/213 |
| 4,392,908 | 7/1983 | Dehnel | 427/194 |
| 4,394,172 | 7/1983 | Scheuble et al. | 106/38.5 D |
| 4,404,250 | 9/1983 | Clarke | 428/220 |
| 4,407,771 | 10/1983 | Betzner et al. | 264/115 |
| 4,408,996 | 10/1983 | Baldwin | 8/490 |
| 4,410,571 | 10/1983 | Korpman | 427/385.5 |
| 4,412,036 | 10/1983 | Pederson et al. | 525/54.26 |
| 4,414,267 | 11/1983 | Coran et al. | 428/288 |
| 4,418,676 | 12/1983 | Iwao et al. | 123/580 |
| 4,424,247 | 1/1984 | Erickson | 428/138 |
| 4,425,126 | 1/1984 | Butterworth et al. | 604/366 |
| 4,426,417 | 1/1984 | Meitner et al. | 428/195 |
| 4,428,843 | 1/1984 | Cowan et al. | 252/8.5 C |
| 4,429,001 | 1/1984 | Kolpin et al. | 428/283 |
| 4,430,003 | 2/1984 | Beattie et al. | 366/173 |
| 4,435,234 | 3/1984 | Hunt | 156/62.4 |
| 4,439,489 | 3/1984 | Johnson et al. | 428/404 |
| 4,444,810 | 4/1984 | Huttlin | 427/212 |
| 4,457,978 | 7/1984 | Wawzonek | 524/14 |
| 4,465,017 | 8/1984 | Simmons | 118/418 |
| 4,467,012 | 8/1984 | Pederson et al. | 428/248 |
| 4,468,264 | 8/1984 | Clarke et al. | 156/62.2 |
| 4,469,746 | 9/1984 | Weisman et al. | 428/289 |
| 4,478,896 | 10/1984 | Barnes et al. | 427/421 |
| 4,486,501 | 12/1984 | Holbek | 428/375 |
| 4,487,365 | 12/1984 | Sperber | 239/8 |
| 4,492,729 | 1/1985 | Bannerman et al. | 428/283 |
| 4,500,384 | 2/1985 | Tomioka et al. | 156/290 |
| 4,510,184 | 4/1985 | Winkler et al. | 427/212 |
| 4,514,255 | 4/1985 | Maxwell et al. | 162/9 |
| 4,532,176 | 7/1985 | Briggs et al. | 428/288 |
| 4,537,767 | 8/1985 | Rothman et al. | 424/78 |
| 4,547,403 | 10/1985 | Smith | 427/196 |
| 4,558,091 | 12/1985 | Hubbard | 524/734 |
| 4,559,050 | 12/1985 | Iskra | 604/368 |
| 4,572,100 | 2/1986 | Schlüter | 118/303 |
| 4,572,845 | 2/1986 | Christen | 427/212 |
| 4,584,357 | 4/1986 | Harding | 525/54.21 |
| 4,592,302 | 6/1986 | Motoyama et al. | 118/303 |
| 4,596,737 | 6/1986 | Werbowy et al. | 428/228 |
| 4,597,930 | 7/1986 | Szal | 264/115 |
| 4,600,462 | 7/1986 | Watt | 156/278 |
| 4,610,678 | 9/1986 | Weisman et al. | 604/368 |

| | | | | | | |
|---|---|---|---|---|---|---|
| 4,615,689 | 10/1986 | Murray et al. ............................ 493/51 | | 0 327 327 | 8/1989 | (EP) . |
| 4,647,324 | 3/1987 | Mtangi et al. ....................... 156/62.2 | | 0 440 472 A1 | 1/1990 | (EP) . |
| 4,648,920 | 3/1987 | Sperber ............................... 156/62.6 | | 0 389 015 | 9/1990 | (EP) . |
| 4,656,056 | 4/1987 | Leuenberger ......................... 427/213 | | 0 392 528 | 10/1990 | (EP) . |
| 4,664,969 | 5/1987 | Rossi et al. ............................ 428/284 | | 0 442 185 A1 | 8/1991 | (EP) . |
| 4,673,402 | 6/1987 | Weisman et al. ..................... 604/368 | | 1 382 716 | 2/1964 | (FR) . |
| 4,673,594 | 6/1987 | Smith .................................... 427/196 | | 1 217 452 | 12/1969 | (GB) . |
| 4,676,784 | 6/1987 | Erdman et al. ....................... 604/368 | | 2189127 | 10/1987 | (GB) . |
| 4,689,249 | 8/1987 | Thygesen .............................. 427/180 | | 61-28422 | 2/1986 | (JP) . |
| 4,722,860 | 2/1988 | Doljack et al. ....................... 428/260 | | WO 88/01316 | 2/1988 | (WO) . |
| 4,746,547 | 5/1988 | Brown et al. ......................... 427/213 | | WO 90/09236 | 8/1990 | (WO) . |
| 4,749,595 | 6/1988 | Honda et al. ......................... 427/213 | | WO 90/11170 | 10/1990 | (WO) . |
| 4,758,466 | 7/1988 | Dabi et al. ............................ 428/283 | | WO 90/11171 | 10/1990 | (WO) . |
| 4,772,443 | 9/1988 | Thornton et al. ..................... 264/119 | | WO 90/11181 | 10/1990 | (WO) . |
| 4,772,492 | 9/1988 | Bouchette ............................. 427/342 | | 92/02424 | 2/1992 | (WO) . |
| 4,788,080 | 11/1988 | Hojo et al. ............................ 427/204 | | | | |
| 4,806,598 | 2/1989 | Morman ................................. 525/63 | | | | |
| 4,818,587 | 4/1989 | Ejima et al. .......................... 428/198 | | | | |
| 4,818,599 | 4/1989 | Marcus ................................. 428/288 | | | | |
| 4,818,613 | 4/1989 | Ohtani et al. ......................... 428/396 | | | | |
| 4,826,880 | 5/1989 | Lesniak et al. ....................... 521/53 | | | | |
| 4,833,011 | 5/1989 | Horimoto ............................. 428/288 | | | | |
| 4,842,593 | 6/1989 | Jordan et al. ......................... 604/360 | | | | |
| 4,872,870 | 10/1989 | Jackson ................................. 604/366 | | | | |
| 4,874,811 | 10/1989 | Borchers et al. ..................... 524/516 | | | | |
| 4,886,697 | 12/1989 | Perdelwitz, Jr. et al. ............. 428/192 | | | | |
| 4,892,769 | 1/1990 | Perdelwitz, Jr. et al. ............... 428/68 | | | | |
| 4,902,565 | 2/1990 | Brook ................................. 428/315.5 | | | | |
| 4,937,100 | 6/1990 | Lanters et al. ........................ 427/212 | | | | |
| 4,943,477 | 7/1990 | Kanamura et al. ................... 428/286 | | | | |
| 4,979,318 | 12/1990 | Cohen ....................................... 36/43 | | | | |
| 4,983,452 | 1/1991 | Daimon et al. ....................... 428/287 | | | | |
| 5,002,814 | 3/1991 | Knack et al. ............................ 428/85 | | | | |
| 5,057,166 | 10/1991 | Young, Sr. et al. ................ 156/62.2 | | | | |
| 5,064,689 | 11/1991 | Young, Sr. et al. ................. 427/202 | | | | |
| 5,128,082 | 7/1992 | Makoui ................................. 264/112 | | | | |
| 5,161,686 | 11/1992 | Weber et al. ......................... 206/440 | | | | |
| 5,217,445 | 6/1993 | Young et al. ......................... 604/381 | | | | |
| 5,225,047 | 7/1993 | Graef et al. ................................ 162/9 | | | | |
| 5,230,959 | 7/1993 | Young, Sr. et al. ................. 428/372 | | | | |
| 5,252,275 | 10/1993 | Sultze et al. .......................... 264/119 | | | | |
| 5,252,340 | 10/1993 | Honeycutt ............................ 424/489 | | | | |
| 5,278,222 | 1/1994 | Stack ..................................... 524/502 | | | | |
| 5,283,123 | 2/1994 | Carter et al. .......................... 428/403 | | | | |
| 5,300,054 | 4/1994 | Feist et al. ............................ 604/378 | | | | |
| 5,300,192 | 4/1994 | Hansen et al. ........................ 162/184 | | | | |
| 5,312,522 | 5/1994 | Van Phan et al. .................... 162/111 | | | | |

FOREIGN PATENT DOCUMENTS

| | | |
|---|---|---|
| 1052156 | 12/1976 | (CA) . |
| 1 632 450 | 12/1910 | (DE) . |
| 489 308 | 1/1930 | (DE) . |
| 1 048 013 | 6/1958 | (DE) . |
| 1 079 796 | 6/1962 | (DE) . |
| 2 048 721 | 6/1971 | (DE) . |
| 2 023 659 | 11/1971 | (DE) . |
| 0 043 040 | 1/1982 | (EP) . |
| 0 084 708 | 8/1983 | (EP) . |
| 0 103 214 | 3/1984 | (EP) . |
| 122042 | 10/1984 | (EP) . |
| 0 160 560 | 11/1985 | (EP) . |
| 0 205 242 | 12/1986 | (EP) . |
| 0 212 618 | 3/1987 | (EP) . |
| 0 306 202 | 8/1987 | (EP) . |
| 0 247 539 | 12/1987 | (EP) . |
| 0 341 951 | 11/1988 | (EP) . |
| 0 301 804 | 2/1989 | (EP) . |
| 0 311 344 | 4/1989 | (EP) . |
| 0 427 316 A2 | 7/1989 | (EP) . |
| 0 427 317 A2 | 7/1989 | (EP) . |
| 0 429 112 A2 | 7/1989 | (EP) . |

OTHER PUBLICATIONS

Byrd, "How bonds develop during web consolidation," *PTI,* pp. 240–243 (Oct. 1986).

Gorbushin et al., "Investigation of the effect of the nature and concentration of binders on the properties of dry–process paper," *Sb. Tr. Tsentr. Nauch.–Issled. Inst. Bumagi,* 9:117–123 (1974).

Gugliemelli et al., "Base–Hydrolyzed Starch–Polyacrylonitrile (S–PAN) Graft Copolymer. S–PAN–1:1, Pan M.W. 794,000*", *J. of Applied Copolymer Science,* 13:2007–2017 (1969).

Hoque et al., "Granulation and Tabletting of Iron Oxide–Chromic Oxide Catalyst Mass with the Aid of Binding Ingredients Part II—Cellulosic Derivatives and Polyethylene Glycol as Binding Ingredients," *Fertilizer Technology,* 20:30–35 (1983).

Lindsay, "Absorbent Starch Based Co–polymers—Their Characteristics and Applications," *Formed Fabrics Industry,* pp. 20, 24 and 26 (May 1977).

Lysogorskaya et al., "Effect of Moisture Content on the Development of Interfiber Bonds in Air–Laid Paper," *Leningrad Technological Institute of the Pulp and Paper Industry,* Zh. Prikl, Khim., 63:(8) 1869–1872 (1990).

Lysogorskaya et al., "Effect of Moisture Content on Development of Interfiber Bonding in the Structure of Air–Dried Paper," *Plenum Publ. Corp.,* pp. 1730–1733 (1991).

Ogurtsov et al., "Effect of the modulus of elasticity of the binder on the properties of dry–process paper," *Sb. Tr. Tsentr. Nauch.–Issled. Inst. Bumagi,* 9:123–127 (1974).

S. Lammie, "Use of Glycerine as a Softener for Paper Products," *The World's Paper Trade Review,* p. 2050, Dec. 13, 1962.

Sliwiok and Kowalska, "Investigation of Self–Association of the Selected Glycols and Cellulose Sorbents," Microchemical Journal, 26:68–74 (Jan. 1992).

"Super slurpers: Time for change?," *Chemical Week,* pp. 21–22 Jul. 24, 1974.

Weaver et al., "Hydrolyzed Starch–Polyacrylonitrile Graft Copolymers: Effect of Structure on Properties*", *J. of Applied Polymer Science,* 15:3015–3024 (1971).

Weaver et al., "Highly Absorbent Starch–Based Polymer," *Northern Regional Research Laboratory, Agricultural Research Service,* U.S. Dept. of Agriculture, Peoria, Illinois, pp. 169–177, Undated.

COATED FIBER PRODUCT WITH ADHERED SUPER ABSORBENT PARTICLES

This is a continuation, of application Ser. No. 07/890,040, filed May 27, 1992, now abandoned, which is a continuation of prior application Ser. No. 07/326,188, filed Mar. 20, 1982 now U.S. Pat. No. 5,230,959, issued Jul. 27, 1993.

BACKGROUND OF THE INVENTION

The present invention relates to discontinuous fibers with a binder material to which super absorbent particulate materials are adhered. The binder may be of a heat fusible material which is applied as a liquid to fibers entrained in a gaseous medium. The particulate super absorbent material is adhered to the fibers by the binder material as the binder material dries and without heat fusing the binder to adhere these particles.

A number of techniques for applying binders to webs of fibers are known. For example, U.S. Pat. No. 4,600,462 of Watt describes a process in which an adhesive binder is sprayed onto one or both surfaces of an air laid cellulose fiber web. Submersion of the web in the adhesive binder is another method disclosed in this patent of applying the binder. Individual binder coated fibers for mixing with other fibers are not produced by this process. A hydrophile solution is also applied to the web. As another example, U.S. Pat. Nos. 4,425,126 and 4,129,132 of Butterworth, et al. describe a fiberous material formed by combining thermoplastic fibers and wood pulp, heat fusing the combined fibers, and thereafter depositing a binder on the heat fused web. Because the fibers are heat fused prior to adding the binder, individual binder coated fibers for mixing with other fibers are not produced by this process.

U.S. Pat. No. 4,584,357 of Harding discloses a latex treated cationic cellulose product and method for its manufacture. In the Harding approach, cationized cellulose is treated in an aqueous suspension with an anionic polymer emulsion of from 0.1 to 30 percent on a dry weight basis. The patent mentions that the resulting resin treated products can be prepared in sheet form, as loose fibers or in another form. The approach of the Harding patent is limited to cationic fibers. Also, the fiber coating applied as described in the Harding patent had a tendency to flake off or separate from the fibers. Moreover, because the Harding approach uses a wet process, the lumen of the cellulose fibers is penetrated by the polymer emulsion. Since the binder on the surface of the fibers contributes principally to the desired characteristics of the fiber, any polymer that penetrates the lumen of the fiber adds little to these desired characteristics.

U.S. Pat. No. 4,469,746 of Weisman et al. discloses fiberous webs comprised of fibers coated with a continuous film of silica. The fibers are understood to be dispersed in a charged silica aquasol to accomplish the coating. Because silica is an inorganic material, the silica does not contribute to subsequent bonding of fibers. In addition, because Weisman et al. discloses a wet process, the silica will tend to penetrate the lumen of cellulose fibers in the event such fibers are being treated in accordance with this patent.

U.S. patent application Ser. No. 067,669, filed Jun. 26th, 1987, and entitled "Treated Wood Fiber Having Hydrophobic and Oleophilic Properties", by Jewell et al., mentions an approach of treating fiberized wood with surfactant material to penetrate the surface of the wood fibers. In this approach, fiberized wood at the outlet of a first fiberizing machine passes through an orifice into a blow line. At the outlet of the fiberizing machine, liquid surfactant is injected into the line. At the point of addition of the surfactant, the fiber is still wet as it has been carried by steam through the fiberizing machine. Surfactants are not suitable for use in subsequent bonding of the fibers. The Jewell et al. patent application also describes a process in which fibers are treated with a copolymer latex, such as a combination of a paraffin wax emulsion and a styrene butadiene copolymer latex. The patent describes a suitable treating process as involving the blending of the aqueous latex emulsion with wood fiber in a typical mechanical wood fiber blender. This approach tends to produce fibers which are bound together by the latex.

U.S. Pat. No. 2,757,150 of Heritage mentions a fiber treatment approach in which fibers are carried by steam under pressure and in which a thermoset resin is introduced into the fiber stream. Other materials (i.e. rosin and wax) are mentioned as being simultaneously introduced into the fiber stream. The patent indicates that such materials penetrate the surface of the fibers. This patent mentions the individualization of these treated fibers. A relatively low concentration of the thermoset resin (i.e. two percent by weight phenol formaldehyde) is specifically described in this patent. At such low concentrations, the resin is in discontinuous random non-interconnected areas (blobs or globules) on the fibers. These treated fibers are typically used in hardboard. In current hardboard resin products produced using the approach of the Heritage patent and known to the inventors, a phenolic resin concentration of from a maximum of five to six percent by weight is used. Even at these concentrations, the resin forms random non-interconnected globules on the fibers. As a result, the uncoated resin free areas of the fibers lack the capacity to bond in comparison to the areas of the fibers covered by the resin. In addition, the untreated surface areas of the fibers may lack desired characteristics of the resin covered areas of the fibers. For example, these uncoated areas may cause the fibers to be more water absorbent than if the entire fiber were coated.

U.S. Pat. No. 4,006,887 of Engels describes a process for treating wood fibers in which the fibers are supported as an annular loose fluidized bed in a mixer which delivers glue by way of shaft mounted mixing rods to the fibers. The patent mentions that radial air vortices are established with the mixer inlet and outlet funnels being connected to an air transport pipe. The patent describes the resulting product as homogenous lump free uniformly coated wood fibers. The patent mentions that the coating of fibers is useful in the manufacture of wood fiber panels. The glue used in the Engels patent and the percentage of the glue that is used is not discussed.

The background portion of the Engels patent describes German Auslegeschrift 1,048,013 as disclosing an impeller or agitator mixer for the coating of wood chips with dusty components. Glue is described as being sprayed through nozzles into a mixing container. An air stream is described as being blown axially through the mixing container in order to reduce the residence time of dusty chip particles to reduce excessive coating of such dusty particles. Also, German Offenlegunge 1,632,450 is mentioned by Engels as disclosing wood chips agitated in an air stream in a mixing tube in which glue spray nozzles are mounted.

Heretofore, synthetic bicomponent fibers have been formed by extruding two materials in air in side-by-side strands which are connected together along their length. Such bicomponent fibers have also been formed with one material being extruded as a concentric sheath surrounding the other material. These extruded strands are then chopped or broken into discontinuous fibers. Although synthetic bicomponent fibers provide good structural efficiency, they are very expensive in comparison to natural fibers, and, therefore, their use is limited.

U.S. Pat. No. 4,261,943 of McCorsley, III describes the extrusion of filaments and the application of a solution of a nonsolvent liquid to the filaments. In this application process, the filaments are passed through a chamber having a nonsolvent vapor laden atmosphere, i.e. a fog of minute particles of nonsolvent. Spraying of the nonsolvent liquid onto the filaments is also mentioned. The approach of the McCorsley, III patent is not understood to apply to discontinuous fibers.

U.S. Pat. No. 4,010,308 of Wiczer describes foamed porous coated fibers. Fibers, described as organic or inorganic fibers of any character, are described as being coated with a foamable plastic material. Thermoplastic and thermosetting coatings are mentioned. In several examples, the coated fibers are made by passing continuous extruded filaments through a first bath of a ten percent polystyrene solution in toluene, evaporating the solvent, and passing the polystyrene coated fiber through a second bath containing a blowing agent, such as liquid n-pentane. The treated filaments are then heated to foam the coating. Rolls are used to rub solid particles into the porous surface of the foam coating. Fireproofing agents, lubricants such as graphite, pigments, and insecticides are among the examples of solid materials mentioned as suitable for rubbing into the coating. In another example, short lengths of cotton linters are described as being wet with a ten percent solution of a copolymer of polystyrene and acrylonitrile in about equal proportions dissolved in benzene. The solvent is evaporated in an air stream and the resulting coated cotton fiber is dipped in mixed pentanes. The product is then stirred in boiling water to cause foaming. Following foaming, the product is centrifugally dried and again dried in an air stream. The fiber is then mixed with a dry powder to fill the pores in the foamed coating with the powder. The placement of this fiber product in a container and heating the product to cause the adherence of the fiber surface contact points is also mentioned. The Wiczer patent appears to use a solution dipping approach as a means of applying the coating to the fibers.

U.S. Pat. No. 4,160,059 of Samejima describes a process in which a natural cellulose fiber (such as wood pulp fiber) is shredded and blended in air with a heat-fusible fiber. The blend is fed to a disintegrator to form supporting fibers to which an absorptive material is added. Heated air is applied to the resulting web to heat the web to a temperature above the melting point of the heat fusible fiber to form bonds between the supporting fibers and absorptive material by heat fusion. Activated carbon black, Japanese acid clay, active alumina, and diatomaceous earth are mentioned as representative absorptive materials. Other powders, including superabsorbents, are also mentioned as being bonded in place in this manner. The background portion of this particular patent also mentions a process in which wood pulp is disintegrated by a dry process, blended with active carbon black, and the blend spread on a wire screen. A binding material such as latex, starch and the like can also be sprayed on both surfaces of the web. With this latter approach, the active surface of the absorptive material is covered with a thin film of the binding material. Thus, under the Samejima approach, heat fusion is used to bind the particles to the fibers. As a result, a bound fiber web, as opposed to individualized fibers, is formed with the particles heat fused to the fibers.

In U.S. Pat. No. 4,429,001 of Kolpin et al., melt-blown fibers are prepared by extruding liquid fiber-forming materials into a high-velocity gaseous stream. The stream of fibers is collected on a screen disposed in the stream with the fibers being collected as an entangled coherent mass. Absorbent particles are introduced into the stream of fibers at the point where the fibers are solidified sufficiently that the fibers will form only a point contact with the particles. The patent mentions that the particles can also be mixed with the fibers under conditions that will produce an area of contact with the particles. The introduction of other fibers besides melt-blown fibers into the resulting sheet product is also mentioned. The patent mentions that surfactants in powder form can be mixed with the sorbent particles used in forming the web or surfactants in liquid form can be sprayed onto the web after it is formed.

Finally, U.S. Pat. No. 4,392,908 of Dehnel describes a process for forming a thermoplastic adhesive resin on a surface of water soluble particles. The coated particles in a dry state are heated and pressed to bond them to a dry substrate (i.e. cellulose fluff). Mixing of absorbent particles with an aqueous latex, spraying resin onto the particles, and mixing the particles in a slurry are mentioned as approaches for coating the particles. Milling of the particles after coating with thermoplastic is mentioned as usually being necessary to produce free flowing particles. Thus, the Dehnel patent illustrates another approach for heat fusing particles to fibers.

Although prior art approaches are known, a need exists for an improved fiber product composed of fibers with a binder material and super absorbent particles adhered to fibers by the binder material.

SUMMARY OF THE INVENTION

In accordance with the present invention, discontinuous fibers have a binder thereon in an amount which is sufficient to produce bicomponent fibers having a substantially continuous layer of the binder material on their surface. The coated fibers are stuck to super absorbent particles by the binder, therefore, the particles are substantially prevented from emigrating or escaping from the fibers. Also, as explained below, the particles and fibers adhere without heat fusing any binder to accomplish this result. A substantial majority of the resulting bicomponent fibers are unbonded to one another, although plural fibers are typically adhered to the same super absorbent particle. By using an organic polymeric material as the liquid binder, and in particular a heat bondable liquid binder material, the fibers with the super absorbent particles may be subsequently heated to fuse them together. The fibers may also be combined with other nontreated fibers and heat fused to provide a bonded web.

In accordance with the method, substantial amounts of binder material may be applied to the fibers with the process still producing individualized coated fibers. However, it has been found that the first binder material must be applied in an amount of at least about seven percent of the combined dry weight of the binder material and fibers in order to produce a substantially continuous binder coating on the fibers. With a substantially continuous coating, little or no surface area of the fibers is exposed and the desired characteristics added to the fibers by the binder material are not nullified or significantly altered by uncoated areas of the fiber. With a binder level of at least about 10 percent of the combined dry weight of the binder material and fibers, and with the binder material being heat fusible, the coated fibers are capable of bonding relatively strongly to one another when heat fused. In addition, binder levels of 30 percent to 50 percent and higher, such as above 90 percent and with no maximum limit yet being determined, can be obtained using the process of the present invention, while still resulting in a product comprised of substantially unbonded individualized fibers. At these higher levels of binder, the treated fibers may readily be mixed or blended with untreated fibers and used in heat fusing the blended fibers. Also, higher binder levels are preferably used to adhere solid super absorbent particulate materials to the fibers.

Super absorbent particulate material is applied to the fibers while the liquid binder material on the fibers is still at least partially wet. As the liquid binder material dries, the super absorbent particulate material is adhered to the fibers.

As another aspect of the present invention, it has also been discovered that binders of the type with free carboxyl groups produce especially strong adhesion of the super absorbent particles and fibers.

In accordance with the method, more than one binder material may be applied to the fibers, such as a thermoset binder material followed by a thermoplastic binder material with the super absorbent particulate material being adhered to the fibers by the binder. Again, substantially individualized fibers containing these plural binder materials can be produced in accordance with the method. Individualized fibers refers to the fibers being substantially unbonded to one another, although they do adhere to the super absorbent particles.

As another feature of the method of the invention, the fibers may be heated following the application of the liquid binder, and after the application of the super absorbent particulate material, to accelerate the drying of the fibers.

Although not as beneficial for many applications, such as when the properties of individual fibers are desired, in addition to individual fibers, fiber bundles may also be included in the fiber product. A fiber bundle is an interconnected group of two or more fibers that are not separated during processing. Fiber bundles, like individual fibers are much longer than wide. For example, when mechanically fiberized wood is produced, some individual fibers result along with fiber bundles of fibers that are not separated during the mechanical fiberization process.

It is accordingly one object of the present invention to provide discontinuous fibers coated with one or more binder materials and with the fibers adhered to super absorbent particles by the binder.

It is another object of the present invention to provide such binder coated fibers which are substantially individualized or unbonded other than to super absorbent particles.

A further object of the present invention is to provide a method of coating discontinuous fibers with liquid binders applied in an amount which is sufficient to substantially continuously coat the fibers or in much higher amounts, the liquid binder adhering the fibers to super absorbent particles.

Another object of the present invention is to provide substantially individualized discontinuous fibers coated with a heat fusible binder material, with super absorbent particulate materials adhered thereto, and in which the binder may be subsequently heated to bond the fibers, with or without additional untreated fibers being added.

A further object of the invention is to form an air laid web directly with dried coated fibers and with partially wet coated fibers.

A subsidiary object of the present invention is to also treat fiber bundles in the same manner as individual fibers are treated.

These and other objects, features and advantages of the present invention will be apparent with reference to the following detailed description and drawings.

DETAILED DESCRIPTION OF THE PREFERRED EMBODIMENTS

Figure 1:
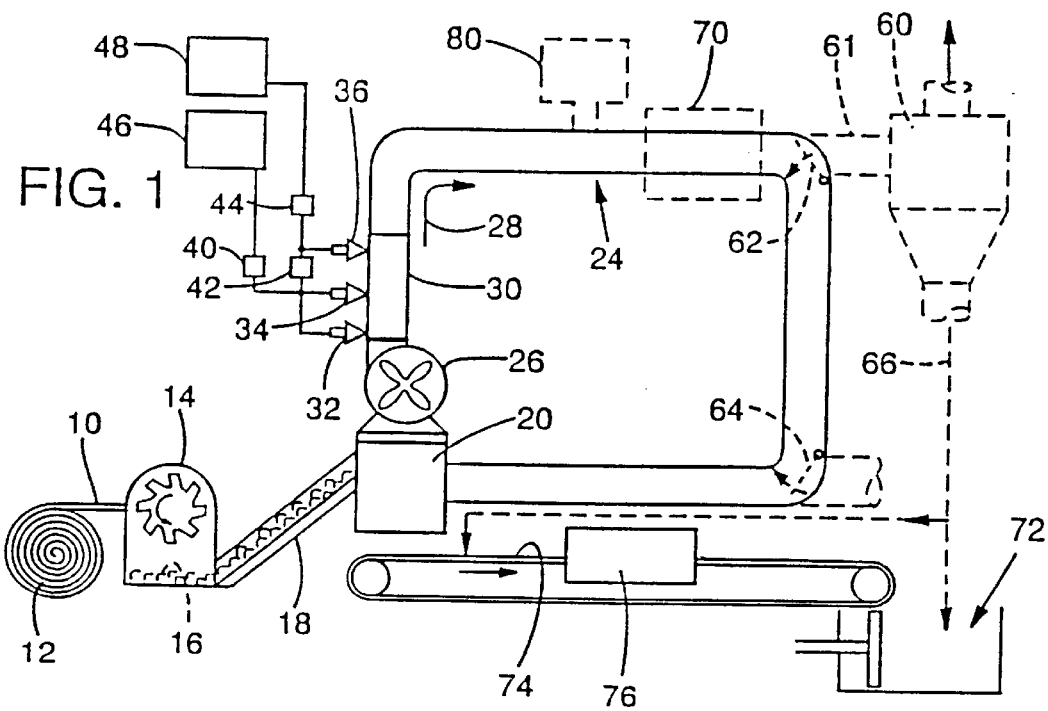
FIG. 1 is a schematic illustration of one form of apparatus in which discontinuous fibers can be treated in accordance with the method of the present invention.

The present invention is a fiber product comprised of treated discontinuous synthetic and natural fibers. The term discontinuous fibers refers to fibers of a relatively short length in comparison to continuous fibers treated during an extrusion process used to produce such fibers. The term discontinuous fibers also includes fiber bundles. The term individual fibers refers to fibers that are comprised substantially of individual separated fibers with at most only a small amount of fiber bundles. Chopped or broken synthetic fibers also fall into the category of discontinuous fibers. Although not limited to any particular type of fiber, the synthetic fibers commonly are of polyethylene, polypropylene, acrylic, polyester, rayon and nylon. Discontinuous fibers of inorganic and organic materials, including cellulosic fibers are also included. The natural fibers may likewise be of a wide variety of materials, with chopped silk fibers, wood pulp fibers, bagrasse, hemp, jute, rice, wheat, bamboo, corn, sisal, cotton, flax, kenaf and the like, and mixtures thereof, being several examples.

Wood pulp fibers can be obtained from well-known chemical processes such as the kraft and sulfite processes. Suitable starting materials for these processes include hardwood and softwood species, such a alder, pine, douglas fir, spruce and hemlock. Wood pulp fibers can also be obtained from mechanical processes, such as ground wood, refiner mechanical, thermomechanical, chemi-mechanical, and chemi-thermomechanical pulp processes. However, to the extent such processes produce fiber bundles as opposed to individually separated fibers or individual fibers, they are less preferred. However, treating fiber bundles is within the scope of the present invention. Recycled or secondary wood pulp fibers and bleached and unbleached wood pulp fibers can also be used. Details of the production of wood pulp fibers are well-known to those skilled in the art. These fibers are commercially available from a number of companies, including Weyerhaeuser Company, the assignee of the present patent application.

For purposes of convenience, and not to be construed as a limitation, the following description proceeds with reference to the treatment of individual chemical wood pulp fibers. The treatment of individual fibers of other types and obtained by other methods, as well as the treatment of fiber bundles, can be accomplished in the same manner.

When relatively dry wood pulp fibers are being treated, that is fibers with less than about 10 to 12 percent by weight moisture content, the lumen of such fibers is substantially collapsed. As a result, when binder materials, in particular latex binder materials, are applied to these relatively dry wood pulp fibers, penetration of the binder into the lumen is minimized. In comparison, relatively wet fibers tend to have open lumen through which binder materials can flow into the fiber in the event the fiber is immersed in the binder. Any binder that penetrates the lumen contributes less to the desired characteristics of the treated fiber than the binder which is present on the surface of the fiber. Therefore, when relatively dry wood pulp fibers are treated, less binder material is required to obtain the same effect than in the case where the fibers are relatively wet and the binder penetrates the lumen.

Binders used to treat the fibers broadly include substances which can be applied in liquid form to entrained fibers during the treatment process. These binder materials are preferably of the type which are capable of subsequently binding the fibers produced by the process to one another or to other fibers during the manufacture of webs and other products using the treated fibers. Most preferably these binders comprise organic polymer materials which may be heat fused or heat cured at elevated temperatures to bond the fibers when the fibers are used in manufacturing products. Also, the binder must be of a type which is suitable for the purpose of adhering the fibers to super absorbent particles.

Suitable binders include polymeric materials in the form of aqueous emulsions or solutions and nonaqueous solutions. To prevent agglomeration of fibers during the treatment process, preferably the total liquid content of the treated fibers during treatment, including the moisture contributed by the binder together with the liquid content of the fibers (in the case of moisture containing fibers such as wood pulp), must be no more than about 45 to 55 percent of the total weight, with a 25 to 35 percent moisture content being more typical. Assuming wood pulp is used as the fiber, the moisture contributed by the wood pulp can be higher, but is preferably less than about 10 to 12 percent and more typically about six to eight percent. The remaining moisture or liquid is typically contributed by the binder. These polymer emulsions are typically referred to as "latexes." In the present application, the term "latex" refers very broadly to any aqueous emulsion of a polymeric material. The term solution means binders dissolved in water or other solvents, such as acetone or toluene. Polymeric materials used in binders in accordance with the present method can range from hard rigid types to those which are soft and rubbery. Moreover, these polymers may be either thermoplastic or thermosetting in nature. In the case of thermoplastic polymers, the polymers may be a material which remains permanently thermoplastic. Alternatively, such polymers may be of a type which is partially or fully cross-linkable, with or without an external catalyst, into a thermosetting type polymer. As a few specific examples, suitable thermoplastic binders can be made of the following materials:

ethylene vinyl alcohol
    polyvinyl acetate
    acrylic
    polyvinyl acetate acrylate
    acrylates
    polyvinyl dichloride
    ethylene vinyl acetate
    ethylene vinyl chloride
    polyvinyl chloride
    styrene
    styrene acrylate
    styrene/butadiene
    styrene/acrylonitrile
    butadiene/acrylonitrile
    acrylonitrile/butadiene/styrene
    ethylene acrylic acid
    polyethylene
    urethanes
    polycarbonate
    polyphenylene oxide
    polypropylene
    polyesters
    polyimides In addition, a few specific examples of thermoset binders include those made of the following materials:

epoxy
    phenolic
    bismaleimide
    polyimide
    melamine/formaldehyde
    polyester
    urethanes
    urea
    urea/formaldehyde As explained more fully below, in accordance with the method of the present invention, more than one of these materials may be used to treat the discontinuous fibers. For example, a first coating or sheath of a thermoset material may be used followed by a second coating of a thermoplastic material. The super absorbent particles are then typically adhered to the outer binder material. During subsequent use of the fibers to make products, the thermoplastic material may be heated to its softening or tack temperature without raising the thermoset material to its curing temperature. The remaining thermoset material permits subsequent heating of the fibers to cure the thermoset material during further processing. Alternatively, the thermoset material may be cured at the same time the thermoplastic material is heated by heating the fibers to the curing temperature of the thermoset with the thermoplastic material also being heated to its tack temperature.

Certain types of binders enhance the fire resistance of the treated fibers, and thereby of products made from these fibers. For example, poly vinyl chloride, poly vinyl dichloride, ethylene vinyl chloride and phenolic are fire retardant.

Surfactants may also be included in the liquid binder as desired. Other materials may also be mixed with the liquid binder to impart desired characteristics to the treated fibers. For example, particulate material, such as pigments, may also be included in the binder for application to the fibers.

In addition, super absorbent particulate materials are adhered to the fibers to provide desired functional characteristics. The solid particulate materials are applied to a binder wetted surface of the fibers and are then adhered to the fibers by the binder as the binder dries. In this case, heat curing or heat fusing of the binder is not required to adhere the particles to the fibers. Thus, the super absorbent particles are not coated with the binder, which could interfere with their optimum liquid absorption. In addition to super absorbent particulate materials, other particulate materials may also be adhered to the fibers. Examples of such other particulate materials include pigments, such as titanium dioxide; fire retardant materials, such as alumina trihydrate and antimony oxide; electrically conductive materials, such as metallic powders and carbon black; abrasive materials, such as ceramics, grit and metallic powders; acidular materials, such as clay, talc and mica, used as papermaking additives; oleophilic materials; hydrophobic materials; and other hydrophilic materials; insecticides; and fertilizers. Thus, the solid particulate materials are not limited to narrow categories.

The super absorbent particulate materials are granular or powdered materials which have the ability to absorb liquids, including body fluids. These super absorbents are generally hydrophilic polymeric materials. Super absorbents are defined herein as materials which exhibit the ability to absorb large quantities of liquids, i.e. in excess of 10 to 15 parts of liquid per part thereof. These super absorbent materials generally fall into three classes, namely, starch graft copolymers, cross-linked carboxymethylcellulose derivatives and modified hydrophilic polyacrylates. Without limiting the generality of the term super absorbent, examples of super absorbents include carboxylated cellulose, hydrolyzed acrylonitrile-grafted starch, acrylic acid derivative polymers, polyacrylonitrile derivatives, polyacrylamide type compounds and saponified vinyl acetate/methyl acrylate copolymers. Specific examples of super absorbent particles are marketed under the trademarks SANWET super absorbent particles (supplied by Sanyo Kasei Kogyo Kabushiki Kaisha) and SUMIKA GEL super absorbent particles (supplied by Sumitomo Kagaku Kabushiki Kaisha).

An abrasive is a hard substance that, in particulate form, is capable of effecting a physical change in a surface, ranging from the removal of a thin film of tarnish to the cutting of heavy metal cross sections and cutting stone. Abrasives are used in scores of different abrasive products. The two principal categories of abrasives are: (1) natural abrasives, such as quartz, emery, corundum, garnet, tripoli, diatomaceous earth (diatomite), pumice, and diamond; and (2) synthetic abrasives, such as fused alumina, silicon carbide, boron nitride, metallic abrasives, and synthetic diamond.

Oleophilic materials are those capable of rapid wetting by oil while hydrophilic materials are those capable of rapid wetting by water.

Pigments or colorants can broadly be defined as being capable of reemitting light of certain wavelengths while absorbing light of other wavelengths and which are used to impart color.

Electrically conductive materials are those which readily conduct electric current.

In addition, fire retardant materials are those which reduce the flammability of the fibers to which they are attached. Preferably these materials are active fire retardants in that they chemically inhibit oxidation or they emit water or other fire suppressing substances when burned.

With reference to FIG. 1, a sheet of chemical wood pulp 10 is unrolled from a roll 12 and delivered to a refiberizing apparatus, such as a conventional hammer mill 14. The sheet 10 is readily converted into individual fibers 16 within the hammer mill. These individual fibers are delivered, as by a conveyor 18, to a fiber loading zone 20 of a fiber treatment apparatus. In the case of a continuous process, fibers 16 are continuously delivered to the zone 20. In a batch or semi-batch process, fibers are loaded at zone 20 at intervals.

In the FIG. 1 fiber treatment apparatus, loading zone 20 forms part of a fiber treatment conduit 24. The illustrated conduit 24 comprises a recirculating loop. A blower or fan 26 in the loop 24 is positioned adjacent to the fiber loading zone 20. Blower 26 is capable of moving a gaseous medium, such as air, at a velocity and volume sufficient to entrain the fibers which have been loaded into zone 20. The entrained fibers circulate in a direction indicated by arrow 28 through the loop and pass through the loading zone 20 and blower 26 each time the loop is traversed.

The velocity of air traveling in the loop is preferably set at a level where solids are uniformly dispersed and transported by the air flow. In addition, the velocity is preferably established at a level which is sufficient to avoid saltation, that is the dropping of solids or liquids from a horizontal air stream. As a specific example, when Type NB316 chemical wood pulp, available from Weyerhaeuser Company, was used as the fiber, a velocity of 5,000 feet per minute worked extremely well for treatment of these fibers. However, this velocity can be varied and adjusted for optimum results.

Also, the ratio of the volume of air per pound of entrained fiber is variable over relatively large ranges. One suitable example is 23.4 $ft^3$ of air per pound of fiber. As another example, 11.7 $ft^3$ of air per pound of fiber produced equivalent results.

The entrained fibers traveling in the loop pass one or more binder material application zones, with one such zone being indicated in FIG. 1 at 30. This binder material application zone 30 forms a part of the conduit 24. A mechanism is provided at the binder application zone for applying a liquid binder solution to the entrained fibers. In the FIG. 1 form of this mechanism, plural nozzles, in this case nozzles 32, 34. and 36, are used to apply the liquid binder material. These nozzles produce an atomized spray or mist of binder drops which impact and coat the fibers as the fibers pass the nozzles.

In the FIG. 1 apparatus, plural valves 40, 42 and 44 are operated to control the flow of liquid binder material to the respective nozzles 32, 34 and 36. In the illustrated configuration, a first liquid binder material from a tank or other source 46 is delivered to the three nozzles 32, 34 and 36 when valves 40 and 42 are open and valve 44 is closed. As the fibers recirculate through the conduit 24, and each time they pass the nozzles, an additional amount of the first liquid binder material is applied. Different surfaces of the fibers are exposed to the nozzles 32, 34 and 36 as the fibers travel through the material application zone 30. After the desired amount of the first liquid binder material is applied, the valve 40 is closed. If desired for a particular application, a second liquid binder material from a tank or other source 48 may also be applied to the fibers. With valves 42 and 44 open and valve 40 closed, this second liquid binder material is applied to the fibers through each of the nozzles 32, 34 and 36. In addition, the two liquid binder materials may be simultaneously applied, at successive locations in zone 30. For example, the valve 42 may be closed and valve 44 opened so that the first liquid binder material is applied through nozzles 32, 34 and the second liquid binder material is applied through nozzle 36. More than two types of liquid binder materials may be applied by adding additional binder sources and suitable valving and nozzles.

In general, the material application zone 30 typically ranges from two to one hundred feet long, with longer application zones allowing the application of binder over a longer period of time during passage of fibers through the material application zone. Also, longer material application zones facilitate the use of more nozzles spaced along the length of the zones.

The nozzles 32, 34 and 36 are commercially available and produce a fine mist of droplets. Typically, these nozzles provide a fan spray. Any suitable nozzles may be used, but it is desirable that the nozzles not produce a continuous stream of liquid binder material, but instead produce droplets or a mist of such material. The nozzles are typically spaced apart from three to four feet along the length of the conduit, although they may be closer or further apart as desired.

Virtually any amount of binder material may be applied to the entrained fibers. However, it has been found that the application of binder must be at a minimum of about seven percent of the dry weight of the combined fibers and binder in order for the fibers to have a substantially continuous sheath or coating of the binder material. If the fibers lack a continuous coating, it becomes more difficult to adhere significant amounts of super absorbent particulate material to the binder in the manner explained below. In fact, a much higher percentage of binder than this minimum is preferably used to adhere these particles and the fibers. Also, exposed portions of the core fiber, that is surface areas of the fiber not coated with the binder, lack the desired characteristics of the binder. For example, if a hydrophobic binder is used to cover a water absorbing cellulose material, failure to completely enclose the material with the coating leaves exposed surfaces of the fiber which can absorb water. Also, any uncoated areas on the fibers would not bond to other untreated fibers during subsequent heat bonding of the treated and untreated fibers.

It has also been found that, with a binder concentration of about 10 percent by dry weight of the weight of the fiber and binder combination, the fibers, when heat fused, will bond somewhat strongly to other fibers coated in a similar manner, but less strongly to untreated fibers. The resulting bond strength is similar to the strength achieved when fibers coated with a 40 percent by dry weight binder amount are mixed with untreated fibers in a ratio of one part treated fiber to three parts untreated fiber. A binder concentration by dry weight of the combined binder and fibers of from 30 percent to 50 percent has proven extremely suitable for use in mixing with other fibers, heat bonding, and use in forming products such as absorbent pads.

Binder concentrations in excess of 50 percent, for example 90 percent or more, can be achieved utilizing the present invention. To achieve these extremely high binder concentrations, one preferred approach is to apply a first amount of the binder material to the entrained fibers, continue to recirculate the fibers until this first layer or coating of binder material is substantially dry, and then apply a second coating of the binder material. Third, fourth and subsequent coatings can be applied to the entrained fibers as necessary to achieve the desired level of binder material.

Following the application of the liquid binder material to the fibers and the super absorbent particulate material as explained below, the fibers may be retained in the loop until they have dried. The recirculation of the fibers may then be stopped and the fibers removed at the loading zone 20, which then functions as a fiber removal location. However, in the FIG. 1 apparatus, a cyclone separator 60 is selectively connected by a conduit section 61 and a gate valve 62 to the conduit 24. At the same time a valve 64 is opened to allow air to enter the loop 24 to compensate for air exiting through the separator 60. With the separator in the loop, the entrained fibers are collected in the separator and then removed from the separator at a fiber removal outlet 66. A substantial majority of the fibers processed in this manner are unbonded to one another by the binder material. By substantial majority, it is meant that at least about 70 percent of the fibers remain unbonded. More specifically, in tests conducted as of this time, the resulting treated fibers are substantially unbonded, meaning that approximately 95 percent of the treated fibers have been found to be unbonded to one another by the binder material. However, plural fibers are bonded to the super absorbent particles.

An optional means for heating the binder coated fibers may be included in conduit 24. For example heated air may be blended with the air flowing through the conduit. Similarly, a heater 70 may be included in conduit 24 for heating the fibers. This added heat accelerates the drying of the liquid binder and adhered super absorbent particles. In the event a thermoplastic heat fusible binder is used, the fibers are preferably heated above the film forming temperatures of the binder and below the hot tack temperature at which the binder becomes tacky so that the binder coated fibers may subsequently be heat fused during processing of the fibers into products. Also, if a thermoset heat fusible binder is used, the fiber temperature is preferably maintained below the curing temperature of the binder so that the binder coated fibers may be subsequently heat cured during the processing of the binder coated fibers into products.

The fibers are preferably not heated prior to the application of the binder material. It has been found that heating the fibers results in elevated temperatures at the binder application zone 30. These elevated temperatures cause some of the binder to at least partially dry (coelesce) before reaching surfaces of fibers passing through the binder application zone 30. The solidified binder tends to either not adhere, or only adhere weakly, to the fibers. In addition, droplets of binder which impinge heated fibers tend to dry in globules on the fibers, rather than spread across the surface of the fibers to provide a substantially continuous uniform coating thereon.

The dried fibers from outlet 66 of the cyclone separator 60 may be deposited in a conventional baling apparatus 72 to prevent bonding of the fibers in the baler, the fibers are at a temperature which is below their curing or tack temperature under the pressure applied by the baler. When compressed, these fibers remain unbonded by the binder material.

Also, treated fibers which have only been partially dried, and thus which are still somewhat wet with the binder material, may be deposited from outlet 66 loosely onto a conveyor 74 or in a loose uncompressed pile at a collecting zone (not shown). These fibers can then be allowed to dry. Alternatively, the treated fibers may be carried by the conveyor 74 through a heater 76, operable like heater 70, to accelerate the drying of the fibers. The resulting product again contains a major portion of unbonded fibers. However, the wetter the fibers and more dense the resulting web when deposited on belt 74, or in a pile, the more binder-to-binder bonds that occur. Thus, in many cases it is preferable to at least partially dry the fibers within the conduit 24 prior to removing the fibers therefrom. However, the fiber may be air laid either dry or wet, that is with no more than about a 55 percent total moisture content in the fibers and binder thereon, directly into a web which can then be processed into various products, such as into disposable diapers with the core of the diaper being formed by the web. Air laying refers to the transfer of the fibers through air or another gaseous medium.

As previously mentioned, super absorbent particles, as well as other solid particulate materials, may be adhered to the fibers by the binder material. Due to the relatively large size of super absorbent particles, plural fibers are in effect adhered to the particles.

To accomplish this, the solid particulate material, such as super absorbent particles, is added to the loop 24, such as at the fiber loading zone 20. The particles may also be added to the loop 24 from a supply housing 80, using a feed screw metering device or other conventional injection mechanism. Preferably, the particles are added after the fibers have been wetted with the binder material. Consequently, the particles will not be covered with the binder material, which could interfere with the desired attributes contributed by the particles. These particles contact the wet binder material on the surfaces of the fibers and stick to the binder material. As the binder material dries, the particles remain stuck to the surface of the treated fibers. In one specific approach, the fibers are treated with a binder, circulation of the fibers is stopped momentarily to allow the addition of the solid particulate material at the fiber loading zone 20, and recirculation and entrainment of the fibers is recommenced. The particles mix with and are secured to the surface of the fibers by the liquid binder material as the binder dries. Although lower concentrations are effective in binding particles to fibers, it has been found that relatively high levels of binder concentrations, for example 20 percent or more of the dry weight of the binder, fiber and additive, produces the best adhesion of particles to the fibers. A 50 percent binder concentration would perform better at adhering particles to the fibers than a 20 percent binder concentration in many applications. These higher binder levels, when heat fusible binders are used, facilitate subsequent heat fusion of the fibers and strong bonding, with or without other fibers being added, during use of the fibers in manufacturing products.

The FIG. 1 apparatus may be operated in a batch mode in which fibers are introduced, fully treated and removed. Alternatively, a semi-batch approach may be used in which fibers are added and some, but not all, of the fibers removed from the loop. Also, the FIG. 1 apparatus may be operated in a continuous mode in which fibers are introduced at zone 20 and removed by the cyclone separator 60 with or without recirculating through the loop. The gate valves 62, 64 may be opened to a desired extent to control the amount of fiber that is removed. This quantity of removed fiber is preferably equal to the amount of untreated fiber that is introduced into the loop. In this nonrecirculating case, the zone 30 is typically expanded.

Figure 2:
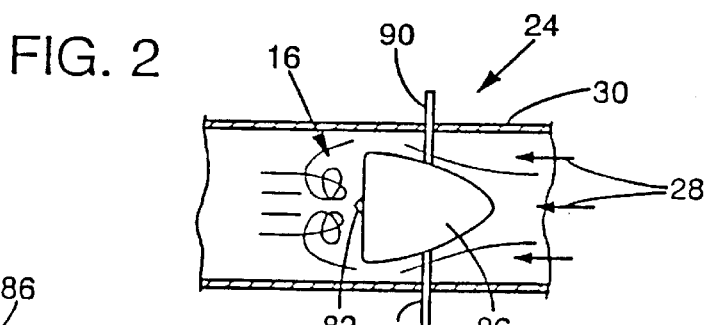
FIG. 2 is a side elevational section view of one form of binder application mechanism which can be used to apply liquid binder material to discontinuous fibers in accordance with the method of the present invention.
Figure 3:
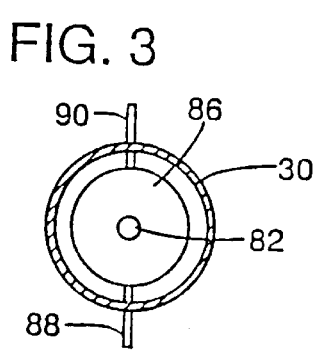
FIG. 3 is a front elevational section view of the binder application mechanism of FIG. 2.

With reference to FIGS. 2 and 3, another mechanism for applying binder material to the fibers is illustrated. Rather than using external spray nozzles such as 32, 34 and 36, plural nozzles (i.e., one being shown as 82 in FIGS. 2 and 3) are included in the conduit at the binder material applying zone 30. The nozzle 82 applies a fine spray of liquid binder material onto the fibers 16 as they move past the nozzle. The FIGS. 2 and 3 binder applying mechanism includes a means for imparting turbulence to the air as it passes the nozzles. As a result, the fibers 16 tend to tumble in front of the nozzles and expose different surfaces to the applied binder material. The illustrated turbulence imparting mechanism comprises a blunted conical air deflection baffle 86 supported within the conduit 24 by rods, with two such rods 88 and 90 being shown. Rod 90 may be hollow to provide a pathway through which binder material is delivered to the nozzle 82. Of course, other turbulence imparting mechanisms may also be used.

Figure 4:
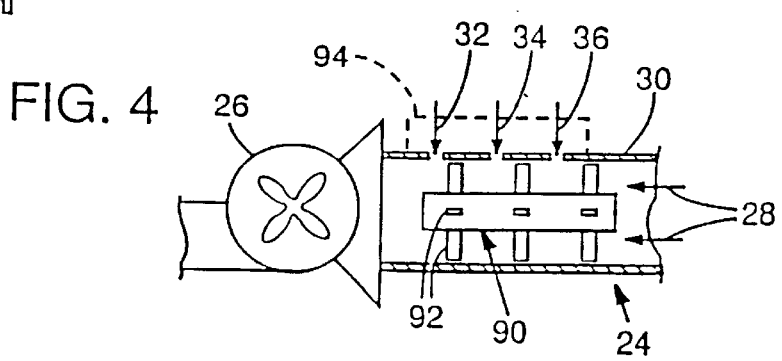
FIG. 4 is a schematic illustration of another form of binder application mechanism which can be used to product the fiber product of the present invention.

In FIG. 4, a rotary mixer 90 with plural mixing paddles, some being indicated at 92, is disposed within the conduit 24 at the material applying zone 30. This mixer is rotated by a motor (not shown) to impart turbulence to fibers as they pass the mixer paddles. The nozzles 32, 34 and 36 are disposed externally of the conduit 24 for directing the binder material through ports to the fibers passing the mixer. These nozzles may be enclosed in a shroud or cover as shown by dashed lines 94 in this figure. However, in the FIG. 4 approach, blower 26 has been shifted to a location downstream from the material applying zone 30. Consequently, the material applying zone is at a relatively low pressure with a slight vacuum being present in the material applying zone relative to the pressure outside the conduit at this zone. Consequently, fibers passing the nozzles 32, 34 and 36 tend to be drawn into the conduit rather than escaping through the binder applying ports. As a result, the nozzles can be positioned outside of the conduit where they are not subject to being clogged by the passing fibers.

Figure 5:
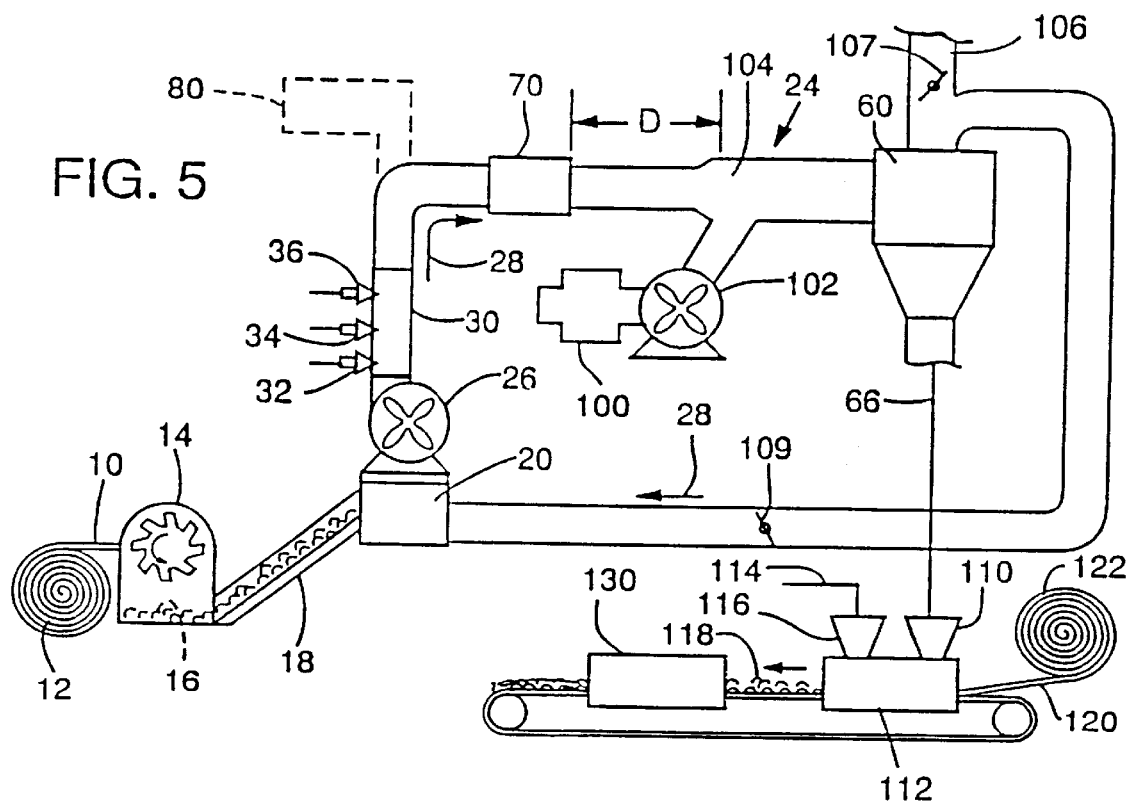
FIG. 5 is a schematic illustration of an alternative apparatus used in producing the fiber product of the present invention.

Referring to FIG. 5, another apparatus is shown for producing the fiber product of the present invention. In FIG. 5, for purposes of convenience, elements in common with those of FIG. 1 have been given like numbers and will not be discussed in detail.

In general, the FIG. 5 form of the apparatus allows the continuous processing of fibers with the fibers passing only once through the binder material application zone 30. However, the zone 30 is typically of an extended length with more nozzles (i.e. six to twelve or more) than shown in FIG. 5. Following the application of the binder material, super absorbent and optionally other solid particulate material may be added from source 80, such as by a blower (not shown) or a feed screw, to introduce the particles into the stream of entrained fibers. The fibers pass through a heater or oven 70, or heated air is blended with the air stream which entrains the fibers, for drying purposes and then travel through a distance D at the elevated temperatures created by this heat. As a typical example, D may be 150 feet with the time required to travel the distance D enabling the binder on the entrained fibers to become substantially dry. Optionally, cooling air from a refrigeration unit 100 or ambient air from the environment may be delivered by a blower 102 to the conduit 24 at a location 104 in the conduit. This cooling air lowers the temperature of the dried and treated fibers. The cooling air may be dehumidified prior to introduction to conduit 24 to minimize any condensation that may otherwise occur in the conduit. Where thermosetting binders are used, preferably the added heat does not elevate the temperature of the fibers to a level which cures the thermosetting binder. Consequently, the binders may subsequently be heat cured when the treated fibers are thereafter used in manufacturing. Also, where thermoplastic binders are used, the temperature is preferably kept above the film forming temperature and below the hot tack temperature of the thermoplastic binder material. Cyclone separator 60 may be provided with a bleed line 106 for venting the air during separation. Although less preferred, this air may be recirculated back to the fiber loading zone 20. Flow control gate valves 107, 109 may be included in the system to balance the air flow through the various conduits of the illustrated system.

The treated fibers from outlet 66 of the separator 60 may be fed to a hopper 110 of a conventional fiber blending unit 112. Other fibers, such as wood pulp fibers or synthetic fibers are fed, in a desired proportion for the resulting product, by way of a conduit 114 to another hopper 116 and then to the blending unit 112. The fibers from outlet 66 can also be used without blending them with other fibers. The blended treated and untreated fibers 118 are shown being deposited on a facing sheet 120 which is passed through the blending unit 112 from a roll 122. The fibers may also be deposited directly on a conveyor without a facing sheet. The facing sheet is carried by a conveyer 124 through the blending unit 112. The composite web is then passed through a thermobonding unit 130 which raises the temperature of the fibers sufficiently to cause the treated fibers to heat fuse to the other fibers and to the facing sheet. The fibers may be compressed to densify the web prior to or after delivery to the thermobonder 130. A cover sheet may also be added to the product before or after the thermobonder 130. Following thermobonding, to reduce the stiffness of the webs, they may be "tenderized" by the use of a mechanism which mechanically breaks up some of the bonds in the web. The web still remains substantially bonded, however. As one example, the webs may be passed through the nips of cross machine direction and machine direction corrugators to reduce their stiffness. The stiffness can be controlled by adjusting the clearance between the nips. Although not limited to a specific approach, examples of suitable corrugators and tenderizing procedures are disclosed in U.S. Pat. Nos. 4,559,050; 4,596,567 and 4,605,402. The resulting material can be used in a conventional manner to manufacture a wide variety of products, such as absorbent pads, disposable diapers, webs and the like.

Figure 6:
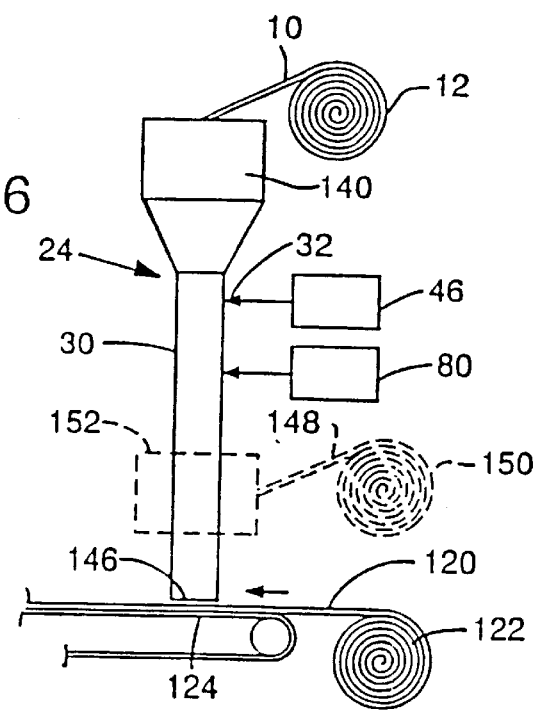
FIG. 6 is a schematic illustration of an apparatus for producing the fiber product of the present invention.

In the FIG. 6 form of apparatus used to produce the fiber product of the present invention, the fibers to be treated may be delivered in loose form or in the form of a sheet 10 from roll 12 to a first hammer mill or refiberizing device 140. The resulting fibers travel through air or another gaseous medium in conduit 24 and through a binder applying zone 30. If the fibers are not conveyed horizontally but merely pass downwardly in the conduit, the air velocity need not be as high. In this sense the fibers are not air entrained, but merely travel through the conduit. At zone 30, a first binder material 46 is applied to the fibers by way of nozzle 32. Again, this is a schematic representation of the apparatus, as plural nozzles are preferably employed and more than one type of binder may be used. Thus, the material applying zone is substantially elongated over that which is shown. Super absorbent particulate material, with or without the optional particulate materials, may also be added to the binder coated fibers from a source of such particles 80. The treated fibers may be air laid or otherwise deposited, wet or dry directly on a face sheet 120 from a roll 122 or directly on a conveyor. Typically a vacuum (not shown) is used to draw the fibers against the screen so that the fibers are not simply falling under the influence of gravity. The face sheet is carried by a conveyor 124 past an outlet 146 of the fiber treatment apparatus. A web of untreated fibers 148 from a roll 150 is optionally delivered to another hammer mill 152 for fiberization and blending with the treated fibers prior to depositing the blend on the face sheet 120. The face sheet 120 and deposited fibers may then be processed, such as previously described, for use in manufacturing a variety of products.

The following examples will serve to more specifically illustrate the method of the present invention, although it is to be understood that the invention is not limited to these examples.

EXAMPLE 1

A bleached Kraft Southern Pine cellulose fiber pulp sheet (NB-316 from Weyerhaeuser Company) was fiberized in a hammer mill. In addition, 1075 grams of the fiberized fluff was then air entrained in a recirculating conduit. After 20 seconds of air entrainment, sufficient PRIMACOR 4990 ethylene acrylic acid copolymer solution (as a 20 percent solids dispersion) was sprayed onto the air entrained fiber over a period of eight minutes. PRIMACOR binder is a hydrophobic, somewhat oleophilic thermoplastic binder. Therefore, a PRIMACOR binder coated fiber is capable of absorbing oil without water. PRIMACOR 4990 binder is available from Dow Chemical Corporation. In addition, a surfactant material was added to the PRIMACOR binder for application with the binder. In this specific example, AEROSOL OT-S Dioctyl Sodium Sulfosuccinate 70.2 percent TS, available from Cyanamid Corporation, was used as the surfactant material. In this example, 1.74 percent surfactant was included based on the Primacor solids.

The loop was then opened and a desired amount of super absorbent particles was deposited onto the damp fluff. A specific example of super absorbent particles is SANWET 1M-1000, available from Celanese Corporation. The coated fiber was then recirculated for twenty seconds prior to removal from the loop. Recirculation of the materials through the loop mixed the particles with the still wet and entrained fibers. Continued circulation of the fibers resulted in partial drying of the binder and adhesion of the particles to the fibers. The still somewhat wet coated fiber was then deposited in a loose pile and air dried at room temperature for 24 hours. With percentages expressed as the percent of the dry weight of the total weight of the fiber, binder and super absorbent particle combination, a number of samples were prepared in this manner, including:

1% PRIMACOR binder 20% super absorbent particles
   2% PRIMACOR binder 40% super absorbent particles
   2% PRIMACOR binder 50% super absorbent particles
   5% PRIMACOR binder 50% super absorbent particles
   10% PRIMACOR binder 50% super absorbent particles
   15% PRIMACOR binder 20% super absorbent particles
   20% PRIMACOR binder 50% super absorbent particles With at least about a 7% binder concentration, a substantially continuous binder coating of the fibers occurred. Even though wood fibers are of irregular cross-section and thus more difficult to coat than surfaces with a regular cross section or smooth surface, the resultant fibers had a uniform continuous coating of binder. Also, approximately 95 percent of the fibers were unbonded to one another by the binder material, although fibers were bonded to the super absorbent particles. The dried fiber was then easily air laid in a laboratory pad former. Observations of the resulting pads confirmed that the binder adhered the fibers to the super absorbent particles, however very little adhesion occurred at binder concentrations below about seven percent. More specifically, it has been found that a binder concentration of 7 percent will adhere some particulate material to the fibers, but at binder concentrations of 20 percent and higher of the total dry weight of the binder, fiber and additives, and higher, much better adhesion occurs. Also, a very uniform distribution of super absorbent particles was present in the resulting web and enhanced the water absorbing characteristics of the web.

It should be noted that the use of surfactants is desirable in many applications, but it not mandatory.

A wide variety of other binders have also been tested, including SYNTHEMUL 40-800 and 40-850 acrylate-acrylonitrile; acrylic and styrene acrylic emulsions, available from Reichhold Chemical Corporation. Cellulose fibers having 5 percent, 7 percent, 10 percent, 20 percent, 30 percent and 50 percent by dry weight SYNTHEMUL 40-800 binder coating have been manufactured using the present method. Again, it is only at levels of about 7 percent that a continuous coating of the fibers is achieved. At 5 percent, the binder material was present as non-interconnected areas or blobs on the surface of the fibers. These percentages are the percent of dry weight of the fiber and binder combination which is the binder. In a recirculating system, to achieve higher percentages of the binder concentration, the fibers were recirculated in the loop during liquid binder application for a longer time. SYNTHEMUL is a more hydrophilic binder than PRIMACOR. Also, ELVACE 40-712 binder, available from Reichhold Chemical Corporation, an ethylene vinyl acetate, has also been tested as have a number of other binder materials. Super absorbent particles in the desired concentration can be adhered by the binding to these fibers. These tests have all confirmed that fibers coated with a substantially continuous coating of binder material and adhered to super absorbent particles can be produced in accordance with the method of the present invention.

Preferably the binders are of a polymeric heat bondable type (for example thermoset or thermoplastic binders) so that they may be subsequently heat bonded, with or without other fibers, in manufacturing a product. However, inorganic materials, such as liquid sodium silicate, in an amount sufficient to provide a substantially continuous coating of the fibers may also be used to adhere particles to the fibers. Although such materials are not used in binding fibers together during subsequent processing, they are capable of binding particles to the fibers and thus in this sense can be called binders. In addition, these materials, when coated on the fibers, add characteristics to the fibers. For example, silicon dioxide increases the wetability of the fibers.

EXAMPLE 2

This example is similar to example 1 in that super absorbent particles are adhered to the fibers by the binder material. Various amounts of super absorbent particles have been successfully adhered to the fibers, including from 15–50 percent of the dry weight of the resultant fiber, binder and additive combination. Lower percentages are also possible as are higher percentages. Again, a specific example of super absorbent particulate material is SANWET 1M-1000, available from Celanese Corporation.

In one more specific example of the method, rather than stopping the fibers to permit addition of the particulate material, super absorbent particles were fed into the air stream containing the entrained fibers immediately following the binder applicaton zone. The resultant material had fiber bonded to the super absorbent particles so as to contain the super absorbent particles in the resultant fluff. Yet, the fibers which were not attached to the particles were substantially unbonded to one another. The dried fluff was then air laid into a web and thermobonded. The web can also be air laid while the binder is wet if desired. The web was tested for absorbency and found to be equivalent to an unbonded product, but with virtually 100 percent containment of the super absorbent particles. In addition, the containment of the super absorbent particles within the fibers prior to thermobonding was also excellent. Again, a very uniform distribution of super absorbent particles was present in the resulting web and enhanced the water absorbing characteristics of the web. Also, the placement of the super absorbent containing particles can be controlled by laying the fibers in a particular portion of the web. With twenty percent and higher concentrations, substantially all of the super absorbent particles were retained in the fiber product. Consequently, the fibers can be stored and transported for subsequent use in products without significant loss or migration of super absorbent particles.

EXAMPLE 3

Thermoset materials may also be used in accordance with example 1 to coat fibers to the desired percentage and to adhere super absorbent particles to the coated fibers. For example, a mixture of polymeric methylene diisocyamate (PMDI) resin, such as PAPI 2027 from Dow Chemical Corporation and propylene carbonate from Arco Chemical Corporation can be sprayed onto the fibers. Dioctyl sodium sulfosuccinate may be used as a surfactant in this case. CASCOPHEN WC04 resin from Borden Chemical Corporation is a specific example of a suitable phenolic resin. Still another example of a specific thermoset resin is CHEMBOND 2509 resin from Chembond, Inc. However, the invention is not limited to specific thermoset binder materials.

Thus, fibers may be introduced into loading zone 20 and entrained. As the fibers travel past the material applying zone 30, nozzles apply the thermoset resin to the fibers. To increase the weight percentage of thermoset resin, the fibers may be recirculated past the nozzles a plurality of times. Also, the lengths of the material zone and number of nozzles may be extended to enhance the rate at which the fibers are coated.

Resin in an amount of about 7 percent of the resin and fiber combination has been found to be required to provide a continuous sheath or coating of thermoset material. Very high weight percentages of thermoset resin, measured in the same manner, can be achieved with 90 percent and higher concentrations expected.

EXAMPLE 4

In accordance with this example, functional materials in particulate form in addition to super absorbent particles can be adhered to the binder coated fibers. These additional particulate materials may be added in the desired percentage in the same manner as the super absorbent particles. For example, these materials may be added to the system at the fiber loading zone 20 or introduced into the stream of entrained binder coated fibers for adhesion by the wet binder to the fibers.

For example, fire retardant particulate materials, such as alumina trihydrate and antimony oxide may be adhered to binder treated fibers for use in preparing fire retardant materials, such as pads, paper and other products.

To produce an electrically conductive material, a conductive particulate material (such as 60–80 percent by weight of the binder fiber and additive combination) may be adhered to the fibers by the binder. Powdered metallic materials and carbon black are examples.

For use in manufacturing abrasive pads and the like, abrasive particulate materials, such as ceramic powders, metallic powders, or grit, may be secured to the fibers by the binder material.

Oleophilic materials, such as polynorbornene in a desired concentration may also be adhered to the fibers. NORSOREX particles from Norsorlor, a division of CdF Chimie of Paris, France, is one example of such a material. Typically, a fugitive surfactant is used in this case. Like the other particulate materials, these materials may be added in varying percentages.

In addition, more than one type of particle may be bound to the fibers if the functional characteristics of more than one particulate material are desired.

EXAMPLE 5

In accordance with this example, the binder can be mixed with a blowing agent, such as Azodicarbonamid, and applied to the entrained fibers with the super absorbent particles.

When the fibers are subsequently heated, nitrogen, carbon dioxide and/or other gases would be released to produce a foamed coating of the fibers. These foam coated fibers can then be used in manufacturing, such as in the manufacturing of low density water absorbing products.

EXAMPLE 6

In accordance with this example, the binder may be a hydrophobic resin or latex material with the particles hydrophilic and the binder may be of a hydrophilic material with the particles hydrophilic. A fugitive surfactant is typically used when water based binders are used and the fibers or particles are hydrophobic.

An example of a hydrophobic binder with a hydrophilic particulate material would be fibers coated with PRIMACOR binder or with PMDI with super absorbent particles adhered to the fibers by the binder. For example, fibers containing a 20 percent PRIMACOR binder, 40 percent by weight super absorbent particles, and 40 percent by weight fiber, have been produced. These percentages are of the total dry weight of the binder, fiber and additive combination. Hexanol surfactants may be used with the binders as previously explained.

Finally, an example of a hydrophilic binder with hydrophilic particles is SYNTHEMUL 40-800 binder as a binder and super absorbent particles as the hydrophilic material.

EXAMPLE 7

The binder may also be comprised of a thermoplastic binder material together with plasticizer particles which cause the polymer to soften when subjected to heat. A specific example of a liquid plasticizer is dioctyl phthalate. A specific example of a particulate plasticizer is sold under the brand name SANTOWAX plasticizer from Monsanto, Inc.

EXAMPLE 8

In accordance with this example, the fibers may be coated with plural binder materials. For example, the first binder material may be a thermoset binder material, such as phenolic resin, which can be applied to the fibers to increase their strength and rigidity. CASCOPHEN WC04 resin is an example of such a resin. This binder can be applied using the apparatus of FIGS. 1, 5 or 6. Following the application of the first binder, a second thermoplastic binder, such as PRIMACOR binder, can be applied to the fibers. This second coating can then be used to bond the super absorbent materials to the fibers that would not bond as strongly to a thermoset coating. During subsequent use of the fibers, they may be heated to the hot tack temperature of the outer binder coating for purposes of heat fusing the fibers. However, because the thermoset coating withstands higher temperatures, its integrity as a fiber and contribution to the strength of the bicomponent fiber remains. Thus, fibers having plural desired characteristics, such as a water repellant undercoating and a highly bondable outer coating, can be produced, with the adhered particulate super absorbent materials.

KRATON binder, a styrene butadiene block copolymer, available from Shell Chemical Corporation is an example of another hydrophobic and oleophilic binder material. This material does not form very strong bonds with other fibers. Therefore, a highly bondable first coating, such as of PRIMACOR binder may be applied to continuously coat the fibers. KRATON binder in a lesser amount may then be applied to only partially coat the fibers. Super absorbent particles may be also adhered to the binder. The exposed PRIMACOR binder coated areas then enhance the bondability of these fibers.

EXAMPLE 9

This example illustrates the applicability of the process to cellulose fibers and fiber bundle material. Specifically, 1111 grams of a mechanically fiberized wood (10 percent moisture) can be placed in a recirculating conduit 24 with an in-line blower. The blower can be turned on to entrain the wood fibers. 952 grams of Reichhold's SYNTHEMUL 40-800 binder (55 percent moisture) can be sprayed onto the fiber through a port in the conduit. After addition of the latex, the super absorbent particles in a desired amount can be added to the still wet fibers and air entrainment recommenced. The treated fiber material can then be shunted out of the loop 24, collected in a cyclone 60 and spread on a bench to air dry.

EXAMPLE 10

It has been found that better adhesion of superabsorbent particles to fiber is achieved if the binder is of a type which has free carboxyl groups. In addition, the higher the percentage of free carboxyl groups in the binder, the greater the observed strength of adhesion of the super absorbent particles to the fibers. Fibers with adhered super absorbent particles were manufactured as explained above in connection with example 1. A comparison of the strengths of adhesion of super absorbent particles was made with PRIMACOR binder as a binder and with SYNTHEMUL 40-504 binder, from Reichhold Chemical Corporation, as a binder. Equivalent amounts of these two binders were used. PRIMACOR binder has a 20 percent carboxylation while SYNTHEMUL 40-504 binder has to 1 to 3 percent carboxylation. In each case the super absorbent particles were adhered to the fibers. However, when these treated fibers were passed through a hammermill, fewer super absorbent particles separated from the fibers treated with the higher carboxyl group containing binder than separated from the fibers treated with the lower carboxyl group containing binder. The carboxyl groups are believed to allow for hydrogen bonding between the particles and the binder.

Having illustrated and described the principles of our invention with reference to several preferred embodiments and examples, it should be apparent to those of ordinary skill in the art that such embodiments of our invention may be modified in detail without departing from such principles. We claim as our invention all such modifications as come within the true spirit and scope of the following claims.

We claim:

1. A fiber product which comprises discontinuous fibers, a binder which coats at least a portion of the fibers, the binder containing carboxyl groups, solid particles of super absorbent material adhered to the fibers by the carboxyl group containing binder, the binder being about seven percent or greater of the combined dry weight of the binder, particles, and fibers to which the super absorbent material particles are adhered by the binder, and wherein the particles are not entirely coated with the binder.

2. A fiber product according to claim 1 in which the binder substantially continuously coats the fibers.

3. A fiber product according to claim 1 in which approximately ninety-five percent of the fibers are not bound together by the binder.

4. A fiber product according to claim 1 in which about seventy percent or more of the fibers are not bound together by the binder.

5. An absorbent article comprised of the fiber product of claim 4.

6. An absorbent article according to claim 5 in which the binder binds the fiber product together.

7. An absorbent article according to claim 1 in which the binder binds the fiber product together.

8. An absorbent article comprised of the fiber product of claim 1.

9. A fiber product according to claim 1 in which the fibers are natural fibers.

10. A fiber product according to claim 1 in which the fibers are cellulosic fibers.

11. A fiber product which comprises discontinuous fibers, a binder which coats at least a portion of the fibers, the binder comprising polymers made from acrylic acid or ethylene acrylic acid containing carboxyl groups, solid particles of super absorbent material adhered to the fibers by the carboxyl group containing binder, the binder being about seven percent or greater of the combined dry weight of the binder, particles, and fibers to which the super absorbent material particles are adhered by the binder, and wherein the particles are not entirely coated with the binder.

12. An absorbent article comprised of the fiber product of claim 11.

13. An absorbent article according to claim 12 in which the binder binds the fiber product together.

14. A fiber product according to claim 11 in which the fibers are cellulosic fibers.

* * * * *